US006423872B2

US006423872B2

(12) United States Patent
Marion

(10) Patent No.: US 6,423,872 B2
(45) Date of Patent: Jul. 23, 2002

(54) CONTINUOUS NI/LOW A1 CATALYZED HYDROGENATION OF AROMATIC NITRO COMPOUNDS

(75) Inventor: Philippe Marion, Vernaison (FR)

(73) Assignee: Rhodia Chimie, Billancourt Cedex (FR)

( * ) Notice: Subject to any disclaimer, the term of this patent is extended or adjusted under 35 U.S.C. 154(b) by 0 days.

(21) Appl. No.: 09/818,507

(22) Filed: Mar. 28, 2001

(30) Foreign Application Priority Data

Mar. 28, 2000 (FR) .............................. 00 03903

(51) Int. Cl.⁷ .............................. C07C 209/36
(52) U.S. Cl. ....................... 564/422; 564/423
(58) Field of Search ................. 564/422, 423

(56) References Cited

U.S. PATENT DOCUMENTS 4,792,626 A    12/1988   Becher et al.

FOREIGN PATENT DOCUMENTS

| FR | 1290268 | 9/1962 |
|----|---------|--------|
| GB | 821220  | 10/1959 |

Primary Examiner—Brian J. Davis
(74) Attorney, Agent, or Firm—Burns, Doane, Swecker & Mathis, L.L.P.

(57) ABSTRACT

Nitrated aromatic compounds are continuously catalytically hydrogenated into their corresponding aromatic amines in the presence of an effective amount of a nickel or nickel/aluminum catalyst, the nickel catalyst being essentially devoid of aluminum values and the nickel/aluminum catalyst containing up to 5.5% by weight of aluminum values; the subject hydrogenation is thus conducted under conditions such as to limit the formation of nickel aluminates and the nickel or nickel/aluminum catalyst is continuously catalytically active for at least three days.

22 Claims, No Drawings

CONTINUOUS NI/LOW Al CATALYZED HYDROGENATION OF AROMATIC NITRO COMPOUNDS

CROSS-REFERENCE TO PRIORITY APPLICATION

This application claims priority under 35 U.S.C. § 119 of FR-00/03903, filed Mar. 28, 2000, hereby expressly incorporated by reference.

BACKGROUND OF THE INVENTION

1. Technical Field of the Invention

The present invention relates to the continuous nickel catalyzed hydrogenation of nitrated aromatic compounds, the nickel catalysts of which optionally comprising low/trace amounts of aluminum values, namely, a content of up to at most 5.5% by weight of aluminum.

This invention more especially relates to such continuous nickel/low aluminum catalyzed hydrogenation of aromatic nitro compounds, which can be carried out for at least three days without any necessity or requirement for replenishing and/or reactivating the catalyst substrate.

2. Description of the Prior Art

Processes for catalytically hydrogenating aromatic nitrated compounds have long been known. In general, these prior art processes are carried out in apparatus usually comprising two zones and peripherals therefor. The first zone is that in which the actual hydrogenation reaction is carried out; the second zone is that in which the catalyst is separated from the reaction mixture and by "peripherals" are intended the pipes, conduits and other apparatus components (storage tanks, recycling tanks, pumps, etc.), by means of which the reaction mixture and/or the reactants are conveyed, and the zone or zones for preparing the reaction mixture. It should be appreciated that the nitrated compounds, fresh solvent, if indeed used, fresh catalyst and a catalyst suspension, emanating from the reaction zone and then the separation zone, are typically admixed in this preparation zone. It is not necessary for the reaction and separation zones to be separate; this because they may exist in the same apparatus, as for example when a reactor/settling tank is employed. The hydrogenation reaction is a very rapid reaction and highly exothermic. It is typically carried out in a stirred reactor, or in a loop reactor. The process of separating the catalyst from the hydrogenate may be carried out in various ways, such as tangential filtration, transverse filtration and settling.

Usually, the hydrogenation processes for aromatic nitrated compounds are carried out in the presence of catalysts comprising at least nickel and aluminum values. Very often the catalyst is of the Raney nickel type. This catalyst may optionally be doped with various metals, such as iron and/or chromium, for example. Such catalysts are obtained via a basic treatment on an alloy comprising the catalyst metal, in this instance nickel, aluminum and possibly dopant metal or metals.

Conventionally, the industrial processes that have been developed employ Raney catalysts whose residual aluminum content is relatively high, on the order of about 7% to 15% by weight of the catalyst.

The advantages of these catalysts are well recognized and deserved, but they present a few drawbacks when employed under conditions such that the reaction is carried out continuously, with long residence times of the catalyst. The same limitations apply if these catalysts are employed under high productivity conditions.

This is because, under such conditions, the parasitic oxidation of the nickel present in the catalyst becomes great. A very hard deposit is then formed over time on the walls of the reactor, of the settling tank and/or of the peripherals. This deposit, which has been identified as having a nickel aluminate structure, for example a lamellar double hydroxide of the takovite type, is due to this significant parasitic oxidation of nickel and to the concomitant presence of hydrated aluminum oxide.

Such deposit creates a screen on the walls of the reactor, the settling tank and the peripherals, thereby reducing the productivity of the process whereas the goal was to in fact increase same.

It is therefore necessary, at quite closely spaced regular intervals, to shut down the plant or the reaction zone in question, and to clean it. However, this operation is very burdensome as it requires the use of relatively powerful means to remove this deposit, such as, for example, high-pressure lances or scraping devices.

SUMMARY OF THE INVENTION

Accordingly, a major object of the present invention is the provision of an improved process for the continuous Ni/low Al catalyzed hydrogenation of aromatic nitro compounds, but which conspicuously avoids or markedly diminishes those disadvantages and drawbacks to date characterizing the state of this art.

Briefly, the present invention features a process for the catalytic hydrogenation of nitrated aromatic compounds, carried out in a reaction zone, a separation zone and peripherals therefor, in which process the hydrogenation is conducted continuously, in the presence of a catalyst which includes at least nickel and possibly/optionally aluminum; the total aluminum content, if aluminum is present, in the catalyst being at most 5.5% by weight of the catalyst. The residence time of the same unchanged catalyst in the reaction zone, separation zone and peripherals can be at least three days without adversely affecting the efficacy and/or productivity of the reaction.

DETAILED DESCRIPTION OF BEST MODE AND SPECIFIC/PREFERRED EMBODIMENTS OF THE INVENTION

More particularly according to the present invention, by the expression "total aluminum" is intended the sum of aluminum (0) values plus aluminum (+III) values.

Thus, it has now been found that by carrying out the hydrogenation under such conditions and by employing a catalyst having, immediately from the beginning of the hydrogenation reaction, a total aluminum content much lower than that present in the catalysts today employed on an industrial scale, or even containing no aluminum in certain cases, the formation of nickel aluminate is greatly diminished, or even eliminated.

The present invention therefore also features the use of a catalyst comprising at least nickel and optionally aluminum, the total aluminum content, if aluminum is indeed present, being at most 5.5% by weight, for the purpose of limiting the formation of nickel aluminates while carrying out the catalytic hydrogenation reaction of aromatic nitrated compounds continuously.

The reduction (or limitation) in the formation of nickel aluminate may especially be observed by the increase by a factor of at least 1.5, preferably at least 2, in the operating time of the process between two shutdowns. It should be appreciated that these shutdowns are necessary since the nickel aluminate deposit then prevents the plant from being operated properly (significant reduction in productivity, blockage of the pipes, especially). Though, when the amount of initial aluminum in the catalyst is low, or when there exists no aluminum whatsoever, it is possible that no shutdown is required between two predetermined stoppages or shutdowns.

In addition, surprisingly, the use of such a catalyst does not significantly degrade the performance of the reaction, especially the yield and the consumption of catalyst. It is even more remarkable to note that the use of this type of catalyst may even help to increase the performance of the reaction.

As one illustration, the process employed under the conditions of the invention makes it possible to achieve a yield of hydrogenated compound (and therefore of aromatic amine) of at least 99.5% by weight.

The catalyst employed in the subject process is particularly suitable for achieving productivities as high as 2 mol of hydrogen converted per hour and per gram of catalyst, or indeed up to 3 mol of hydrogen converted per hour and per gram of catalyst. More particularly, the productivities attained by the process according to the invention range from 0.1 to 3 mol of hydrogen converted per hour per gram of catalyst, preferably from 0.2 to 2 mol of hydrogen converted per hour per gram of catalyst.

Too, the process according to the invention makes it possible to employ, in this reaction, catalysts comprising nickel emanating from other hydrogenation processes such as, for example, those employed for hydrogenating compounds comprising nitrated functional groups or nitrites, or even emanating from the regeneration of catalysts employed in the same process.

Lastly, it has also been found that the catalysts employed in the process according to the invention, even under high productivity conditions, were deactivated less rapidly than the conventional catalysts employed under the same conditions. This is because the pores of the catalysts having a lower aluminum content become blocked less rapidly.

As indicated above, the process according to the invention particularly relates to the hydrogenation of aromatic nitrated compounds in the presence of a catalyst comprising nickel and aluminum.

In one embodiment of the invention, the catalyst has a total aluminum content of at most 5.5% by weight of the catalyst. It should be noted that the catalyst has this maximum aluminum content initially, namely, before it is actually used in the hydrogenation reaction.

In a preferred embodiment of the invention, the total aluminum content is greater than or equal to 1% by weight with respect to the total weight of the catalyst.

Preferably, the total aluminum content ranges from 1% to 5.5% by weight with respect to the total weight of catalyst. Even more advantageously, the total aluminum content in the catalyst ranges from 2% to 5% by weight with respect to the total weight of the catalyst.

In another embodiment of the invention, the catalyst is obtained from an alloy based on nickel, aluminum and optionally at least one dopant (Raney alloy).

Among the conventional dopants in this field, exemplary are the metals of Groups IVA, VA, VIA, VIII of the Periodic Table of Elements (Supplement to the Chemical Society of France Bulletin No. 1, January 1966). Preferably, the dopant is selected from among titanium, iron and chromium, or a mixture thereof.

Catalysts of this type are available from various sources.

From one source, a catalyst is used which is from the alkaline treatment of an alloy comprising aluminum, nickel and optionally at least one dopant, the nature of the alloy and/or the conditions under which the alloy is manufactured and/or the conditions under which the alkaline treatment is carried out having the consequence that the total aluminum content thereof does not exceed 5.5% by weight of the catalyst.

The alkaline treatment may, advantageously, be carried out as follows:

First, the alkaline compound is, in general, a hydroxide of an alkali metal, such as lithium, sodium, potassium, cesium and/or rubidium.

This treatment may, for example, be carried out using an excess of alkaline compound with respect to aluminum. More particularly, said alkaline compound may be employed in an amount such that the molar ratio of alkaline compound to the number of mol of aluminum present ranges from 1.5 to 10. Preferably, said ratio is from 1.5 to 3.

Moreover, it is conventional to employ the alkaline compound in the form of an aqueous solution. More particularly, the concentration of the alkaline compound at the beginning of the treatment ranges from 10% to 50% by weight. Preferably, said concentration is from 15% to 30% by weight.

Advantageously, and for safety reasons, the alkaline treatment is carried out under conditions such that the hydrogen content in the gas phase remains below the lower explosivity limit of the air/hydrogen mixture.

Such conditions may be obtained, for example, by carrying out this treatment under a stream of air or an inert gas such as, inter alia, nitrogen.

It should also be noted that the pressure at which the alkaline treatment is carried out is more particularly greater than or equal to the saturation vapor pressure of the liquid medium at the temperature of the alkaline treatment.

It will be appreciated that this liquid medium comprises, inter alia, water, dissolved aluminum salts and the alkaline compound.

In addition, by the term "saturation vapor pressure" is intended the partial pressure of the liquid medium at the temperature in question.

Furthermore, the temperature at which the alkaline treatment is carried out preferably ranges from 50° to 130° C. Advantageously, the treatment is carried out at a temperature of from 60° to 90° C.

Too, the treatment temperature may change during the alkaline treatment. More particularly, it may be advantageous to increase the temperature at the end of the treatment.

As regards the duration of the alkaline treatment, this more particularly ranges from 1 to 12 hours. Usually this duration is from 1 to 3 hours.

Finally, it should be noted that the aforementioned conditions are selected such that the aluminum remains in a soluble state, especially as an aluminate, during the alkaline treatment to permit same to be separated from the remaining solids after the treatment.

In one embodiment, a catalyst precursor alloy is used having a high aluminum content. For example, alloys having an aluminum content greater than 50% by weight of the alloy are suitable according to the invention.

More particularly, such alloys have an aluminum content of less than or equal to 70% by weight of the alloy, preferably from 55% to 70% by weight of the alloy. Nonetheless, it is also within the scope of the present invention to use alloys whose aluminum content is greater than 70%. Simply, though, the use of this type of alloy may incur unnecessary additional costs during its treatment (cost of the raw material (alkaline compound) and effluent treatment cost).

According to one advantageous embodiment of this first possible route, and if a dopant is present in the precursor alloy, it is preferred to carry out the treatment on an alloy whose dopant content does not exceed 5% by weight of the alloy and preferably does not exceed 3% by weight of the alloy, A second option entails carrying out the alkaline treatment of the precursor alloy under conditions of a higher level than those indicated with respect to the alkaline treatment described above. Thus, among the conditions indicated above, all that is required is for at least one of the conditions to be at a greater level in order for the treatment to be regarded as being carried out at a higher level. For example, these conditions may include a higher alkaline compound/Al molar ratio, and/or a higher initial concentration of the alkaline compound, and/or a higher temperature maintained during the treatment or temperature at the end of the treatment, and/or a longer duration.

In one embodiment of this second option, an additional alkaline treatment can be carried out, i.e., at least one other alkaline treatment is carried out on the product resulting from the first alkaline treatment of an alloy, to further reduce the residual aluminum content.

Thus, a first alkaline treatment may be carried out under conventional conditions and a second treatment under conditions at a higher level, as indicated above.

Likewise, the second treatment may be carried out under conditions similar to those of the first treatment A third option entails employing a catalyst from an alloy that has undergone a particular treatment during its manufacture. Thus, it is possible to employ catalysts obtained from an alloy that has been subjected to an annealing step.

More particularly according to this third option, the alloy ingot is subjected to a heat treatment at a temperature remaining below the peritectic temperature which results in the formation of $NiAl_3$. More particularly, the temperature used in this heat treatment ranges from 650° to 850° C.

Advantageously, this treatment is carried out under an inert atmosphere.

This treatment rearranges the structure of the alloy and promotes the formation of phases rich in aluminum, such as $NiAl_3$ or the eutectic phase, for example. However, the aluminum can be easily removed from such phases during the alkaline treatment for obtaining the actual catalyst.

Of course, it is also within the scope of the present invention to employ a combination of the three aforementioned options.

Another source of catalyst is from the recycling of catalysts that have been used in hydrogenation processes, which may or may not be different from that in which the catalyst is employed.

By way of illustration, the catalysts of the Raney nickel type, doped or undoped, employed in the hydrogenation of compounds comprising nitrated functional groups or nitrites may be suitable for this embodiment. The consumption of the catalysts during such hydrogenation reactions results, among other things, in a significant decrease in the residual aluminum content.

Before it is used in the process according to the invention, the catalyst is advantageously subjected to a first washing operation with water to remove any trace of organic compounds present during the previous operation. The resulting catalyst then is subjected to a regeneration step entailing conducting at least one alkaline washing operation. The purpose of this operation is to remove all or some of the oxidized aluminum values present in the catalyst.

The conditions detailed above for the alkaline treatments may be employed in this type of washing.

However, in another embodiment of this invention, the alkaline washing is carried out at a temperature of less than or equal to 150° C., although higher temperatures may be employed depending on the type of apparatus used and the energy sources available. More particularly, the temperature is advantageously greater than or equal to 50° C., preferably ranging from 80° to 140° C.

The alkaline washing may be carried out at atmospheric or higher pressure, depending on the characteristics of the apparatus utilized. It should be appreciated that there is no significant advantage in carrying out the treatment at total pressures greater than $30 \times 10^5$ Pa.

With regard to the alkaline compound, this is advantageously employed at a concentration of less than or equal to 35% by weight in water.

This regeneration step may also be carried out advantageously under a hydrogen pressure to possibly further reduce a fraction of the oxidized nickel.

In such instance, the treatment is carried out more particularly with a hydrogen partial pressure of at least $10^5$ Pa (1 bar). The hydrogen partial pressure may be as high as possible, depending on the equipment employed. However, this hydrogen partial pressure is advantageously less than or equal to $30 \times 10^5$ Pa (30 bar). The total pressure in the case of a treatment in hydrogen advantageously ranges from 6 to $30 \times 10^5$ Pa (6–30 bar).

Another embodiment of this invention entails the use of catalysts comprising nickel and aluminum, deposited onto a support therefor.

The nickel may optionally be combined with at least one dopant metal such as those belonging to Groups IVA, VA, VIA, VII of the Periodic Table of Elements, preferably titanium, iron or chromium, or a mixture thereof.

Said support is more particularly selected such as to be stable under the reaction conditions.

More particularly, the support advantageously comprises aluminum (more especially in the form of alumina) combined with at least one oxide as zirconium, titanium or silicon, whether by themselves or as mixtures.

Nonetheless, the catalyst is such that the total aluminum content thereof, whatever its degree of oxidation, satisfies the conditions indicated above, namely, it does not exceed 5.5% of the total weight of the catalyst.

The amount of support more particularly ranges from 25% to 80% by weight of catalyst, preferably from 30% to 65% by weight of catalyst.

This type of catalyst is usually obtained by precipitating onto the support a nickel salt and optionally at least one salt of a dopant metal. The catalyst is then separated, for example by filtration, then dried and calcined at a high enough temperature to convert the nickel hydroxide, and perhaps the salt or hydroxide of the dopant metal, into oxides. Once this step has been carried out, the catalyst is subjected to a treatment during which some of the nickel is reduced. This reduction is generally carried out at high temperature in a reducing atmosphere, such as hydrogen.

It would be possible to employ, in the reaction according to the invention, a supported catalyst, i.e., that just described, which had been utilized beforehand in another hydrogenation process. In such event, it is preferable, before the spent catalyst is used at all in the process according to the invention, to conduct a water washing step, or even an alkaline washing step, to remove any trace of organic compounds emanating from the previous process. After this washing step, it is recommended to carry out a reduction treatment, preferably at high temperature in a reducing atmosphere such as hydrogen.

In another embodiment of the invention, the catalyst comprises nickel but not aluminum.

According to this embodiment, the catalyst employed comprises a support which contains no aluminum. The description indicated above with regard to supported catalysts comprising aluminum (preparation; origin (fresh or recycled), treatment of the recycled catalyst before it is introduced into the hydrogenation process according to the invention) remains valid for this embodiment given that aluminum is not present therein.

The catalyst indicated immediately above is therefore employed in a reaction involving the catalytic hydrogenation of nitrated aromatic compounds, carried out continuously.

According to an important feature of the process according to the invention, the residence time of use of the catalyst is at least 3 days.

Consistent with the present invention, the residence time ($T_{res}$) is defined as follows:

The process according to the invention is highly advantageously carried out in a mixture of dinitrotoluene isomers.

The aromatic nitrated compounds may be employed in the presence of a solvent for said compounds.

In a first embodiment, the solvent employed is selected from among aliphatic alcohols or cyclic ethers, whether alone or in admixture.

More particularly, methanol, ethanol, propanol or isopropanol, either alone or in admixture are exemplary aliphatic alcohols.

And exemplary cyclic ethers include dioxane and tetrahydrofuran, also either alone or in admixture.

In this embodiment of the invention, before the aromatic nitrated compounds are introduced into the reaction zone they are dissolved in the above solvents or solvent admixtures.

The concentration of nitrated compounds in the solvent or solvent mixture may vary over a wide range. However, single-phase mixtures, namely, mixtures for which the solubility limit of the nitrated compound or compounds is not reached for the solvent or mixture in question, are used. Without intending to be limited thereby, the concentration range is advantageously less than or equal to 25% by weight.

According to yet another preferred embodiment of the invention, the solvent employed is the hydrogenated compound. In this embodiment, the aromatic nitro compounds are introduced in the liquid or molten state.

This embodiment is advantageous in that it does not dilute the reactant, as is the case when a solvent or solvent mixture $$T_{res} = \frac{\text{Catalyst employed}}{\text{Catalyst consumed} \times \text{Aminated compound production}}$$

| | |
|---|---|
| Catalyst employed: | Amount of catalyst in the reaction zone, separation zone and peripherals, expressed in kg; |
| Catalyst consumed: | Amount of catalyst consumed in the process (amount of catalyst which is purged and not subsequently reinjected into the process); expressed in kg of purged catalyst per metric ton of aminated compound produced; |
| Aminated compound production: | Amount of aminated compound produced, expressed in metric tons per day. |

Very often, the residence time of the catalyst in these zones is on the order of several weeks.

By the term "nitrated aromatic compounds" are intended, in particular, compounds comprising at least one nitrated functional group, and preferably at least two nitrated functional groups, and at least one $C_{6-C14}$, preferably $C_{6-C10}$ aromatic basic nucleus, which may or may not be substituted with one or more $C_{1-C10}$ linear, cyclic or branched, saturated or unsaturated, hydrocarbon radicals and/or one or more hydroxyl radicals.

More specifically, the aforesaid optional hydrocarbon radical substituents borne by said aromatic basic nuclei may be selected from $C_{1-C10}$, preferably $C_{1-C6}$, alkyl, aryl, alkylaryl and arylalkyl radicals.

Exemplary aromatic basic nuclei include, especially, benzene rings and naphthalene rings, which may or may not be substituted with one or more methyl, ethyl, propyl, butyl, pentyl or hexyl radicals and/or isomers thereof.

The process according to the invention may be carried out in a reaction medium comprising at least one compound selected from among mononitrobenzene, dinitrobenzene, mononitrotoluene, dinitrotoluene, paranitrocumene or orthonitrophenol.

is employed. This helps, in particular, to maintain a high process productivity. Moreover, this embodiment obviates any additional step of separating the products from the solvent(s) used during the reaction, which step runs the risk of loss of hydrogenated products.

The instantaneous content of nitrated compounds in the reaction zone is maintained as low as possible. Usually, measures are taken to ensure that it does not exceed 1,000 ppm. This content of nitrated compounds in the reactor is maintained by adjusting the feed rate of nitrated starting compounds such that they are essentially instantly reduced by the catalyst as soon as they are introduced into the reactor. The process according to the invention is very suitable for operating at very high productivity levels, i.e., the aromatic nitrated compound is introduced almost at the maximum rate at which it can be accommodated by the reactor/catalyst pair.

The hydrogen employed is more particularly pure hydrogen. By the expression "pure hydrogen" is intended a gas containing at least 99% hydrogen and more especially at least 99.9% hydrogen. It should be appreciated that it would not be outside the scope of the present invention to carry out the hydrogenation reaction with diluted hydrogen, although this provides no particular advantage.

Preferably, the hydrogen is introduced in the stoichiometric amount. However, it is also intended to carry out the hydrogenation with hydrogen in an excess amount compared with stoichiometry. Such conditions may be advantageous for meeting hydrodynamic criteria, more particularly for optimizing gas/liquid transfer parameters of certain technologies.

The hydrogen pressure in the reactor advantageously ranges from 5 to $70 \cdot 10^5$ Pa (5 and 70 bar), preferably from 10 to $50 \cdot 10^5$ Pa (10 and 50 bar).

This gas is charged by any means known to this art for enabling the gas to be distributed homogeneously within the reactor.

Preferably, the reaction is carried out in a stirred reactor, or in a loop reactor.

The temperature of reaction more particularly ranges from 50° to 200° C.

After the hydrogenation reaction is complete, the reaction mixture is separated from the catalyst by settling or filtration, using conventional techniques.

Of course, the amount of reaction mixture separated corresponds to the amount of nitrated compound, optionally in the presence of the solvent, introduced into the reaction zone, such as to maintain stable operating conditions.

The reaction mixture separated from the catalyst is then treated according to its composition and its subsequent intended use.

Thus, if the reaction is carried out using a solvent, the hydrogenated amino product obtained is separated, for example, by distillation. It will be appreciated that, depending on the choice of solvent and the subsequent step to which the hydrogenated products will be subjected, this separation step may be unnecessary.

Next, the aromatic hydrogenated product can be employed in a phosgenation reaction, after being dehydrated, to obtain aromatic isocyanates, which are intermediates in the production of polyurethanes, or else, if necessary, distilled in order to separate the various isomers obtained.

In order to further illustrate the present invention and the advantages thereof, the following specific examples are given, it being understood that same are intended only as illustrative and in nowise limitative.

EXAMPLE 1

A standard undoped Raney nickel containing 8% total aluminum by weight was evaluated using two tests (Test 1 and Test 2).

(a) Test 1:

50 g/h of a mixture of dinitrotoluene (DNT) isomers were introduced continuously into a reactor containing 0.7 g of Raney nickel at 150° C. under a hydrogen pressure of 20 bar.

The DNT feed was continued until the DNT content in the reactor exceeded 1,000 ppm.

The hydrogen feed was determined by the progress of the reaction in order to remain at constant pressure in the reactor.

The reaction was terminated after 6 hours (h).

The yield of the reaction at t=4 hours was about 99%.

(b) Test 2:

A sample of the initial catalyst (not having been subjected to the hydrogenation) was introduced with a mixture of toluenediamine (TDA) isomers and water into a glass tube termed a Carius tube, which was sealed and then maintained for 1 month at 150° C. under autogenous pressure.

After one month, the tube was opened; the catalyst was irrecoverable and extremely hard.

The structure of the catalyst was determined by X-ray diffraction to be that of a nickel aluminate (takovite). This structure was the same as that of the deposit (screen) observed on the walls of apparatus utilized on an industrial scale.

EXAMPLE 2

The catalyst employed was a Raney nickel recovered from a nitrile hydrogenation unit containing 3.5% total aluminum by weight. The catalyst was first washed with water and then dilute (1N) sodium hydroxide and then again with water. The catalyst was then evaluated employing the same tests as those described in Example 1.

(a) Test 1:

Test 1 of Example 1 was repeated.

The results were as follows:

(i) the reaction was terminated after 8 hours;

(ii) the reaction yield at t=4 h was 99.2%.

(b) Test 2:

Test 2 of Example 1 was repeated.

The results were as follows:

(iii) the tube was opened after 1 month; the catalyst was recoverable and only slightly hard.

Using X-ray diffraction, the structure of the catalyst was basically that of nickel. It contained a small proportion of nickel aluminate (at least half the amount as that in the catalyst of Example 1).

EXAMPLE 3

The catalyst employed in this example was an undoped nickel-based supported catalyst containing about 2% total aluminum by weight, in the form of alumina, 2 to 6% $ZrO_2$, silica and nickel with a total nickel content of 55% by weight.

The catalyst was evaluated using the same tests as those described in Example 1.

(a) Test 1:

Test 1 of Example 1 was repeated.

The results were as follows:

(i) the reaction was terminated after 9 hours;

(ii) the reaction yield at t=4 h was close to 99.2%.

(b) Test 2:

Test 2 of Example 1 was repeated.

The results were as follows:

(iii) when the tube was opened, after 1 month, the catalyst was recoverable and not hard.

Using X-ray diffraction, the structure of the catalyst was found to be basically the same as that observed in the fresh catalyst.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the catalytic hydrogenation of a nitrated aromatic compound, comprising continuously catalytically hydrogenating said nitrated aromatic compound substrate in the presence of an effective amount of a nickel catalyst therefor that is essentially devoid of aluminum, said nickel catalyst being continuously catalytically active for a period of time of at least three days.

2. A process for the catalytic hydrogenation of a nitrated aromatic compound, which comprises continuously catalytically hydrogenating said nitrated aromatic compound substrate in the presence of an effective amount of a nickel/aluminum catalyst therefor, said nickel/aluminum catalyst comprising up to 5.5% by weight of aluminum.

3. The process as defined by claim 2, said nickel/aluminum catalyst comprising at least 1% by weight of aluminum.

4. The process as defined by claim 3, said nickel/aluminum catalyst comprising from 2% to 5% by weight of aluminum.

5. A process for the catalytic hydrogenation of a nitrated aromatic compound, which comprises continuously catalytically hydrogenating said nitrated aromatic compound substrate in the presence of an effective amount of a nickel/aluminum catalyst therefor, said nickel/aluminum catalyst comprising up to 5.5% by weight of aluminum and said nickel/aluminum catalyst being continuously catalytically active for a period of time of at least three days.

6. The process as defined by any of claims 1, 2 or 5, carried out in apparatus comprising both a reaction zone and a reaction product separation zone.

7. The process as defined by claim 2, said nickel/aluminum catalyst comprising at least one dopant.

8. The process as defined by claim 7, said at least one dopant comprising a metal of Groups IVA, VA, VIA and/or VIII of the Periodic Table.

9. The process as defined by claim 8, said at least one dopant comprising titanium, iron and/or chromium.

10. The process as defined by claims 1 or 2, said nickel or nickel/aluminum catalyst being deposited onto effective amount of a support substrate therefor.

11. The process as defined by claim 10, said support substrate comprising aluminum oxide and at least one of zirconium oxide, titanium oxide, and/or silicon oxide.

12. The process as defined by claim 10, said support substrate comprising essentially no aluminum.

13. The process as defined by any of claims 1, 2 or 5, carried out at a temperature ranging from 50° to 200° C.

14. The process as defined by claim 13, carried out under a pressure of from 5 to 70·$10^5$ Pa.

15. The process as defined by claim 14, carried out as to provide a productivity of at most 3 mols of converted hydrogen per hour and per gram of catalyst.

16. The process as defined by claim 15, carried out as to provide a productivity of at most 2 mols of converted hydrogen per hour and per gram of catalyst.

17. The process as defined by claim 15, said nitrated aromatic compound comprising at least two nitro functional groups.

18. The process as defined by claim 15, said nitrated aromatic compound comprising at least one $C_6-C_{14}$ aromatic nucleus optionally substituted with one or more $C_1-C_{10}$ linear, cyclic or branched, saturated or unsaturated, hydrocarbon radicals and/or one or more hydroxyl radicals.

19. The process as defined by claim 15, carried out in the presence of a solvent for said nitrated aromatic compound.

20. The process as defined by claim 19, said solvent comprising an aliphatic alcohol, cyclic ether, or mixture thereof.

21. The process as defined by claim 19, said solvent comprising the aromatic amino product of hydrogenation of said nitrated aromatic compound.

22. The process as defined by claim 15, carried out as to provide a yield of hydrogenated aromatic amine compound of at least 99.5% by weight.

* * * * *